United States Patent [19]
Casperson et al.

[11] Patent Number: 6,156,076
[45] Date of Patent: *Dec. 5, 2000

[54] TWO-PART HAIR DYE COMPOSITIONS CONTAINING POLYETHER POLYURETHANES AND CONDITIONING AGENTS

[75] Inventors: Stephen Casperson, Milford; Bryan Murphy, Monroe; Zubaida S. Khan, Stratford, all of Conn.; Stanley Pohl, Scarsdale, N.Y.

[73] Assignee: Bristol-Myers Squibb Company, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/008,209

[22] Filed: Jan. 16, 1998

[51] Int. Cl.$^7$ ...................................................... A61K 7/13

[52] U.S. Cl. ............................ 8/406; 8/408; 8/410; 8/411; 8/412; 8/552; 8/606; 424/70.6; 424/70.11; 424/70.17

[58] Field of Search ................................ 8/406, 408, 410, 8/411, 412, 552, 606; 424/70.6, 70.11, 70.17

[56] References Cited

U.S. PATENT DOCUMENTS

| | | | |
|---|---|---|---|
| Re. 33,786 | 1/1992 | Pohl et al. .................................. | 8/406 |
| 4,155,892 | 5/1979 | Emmons et al. ......................... | 524/507 |
| 4,180,491 | 12/1979 | Kim et al. ................................. | 524/317 |
| 4,402,700 | 9/1983 | Feinland et al. ............................ | 8/416 |
| 4,496,708 | 1/1985 | Dehm et al. ............................... | 528/76 |
| 4,776,855 | 10/1988 | Pohl et al. .................................. | 8/406 |
| 5,100,658 | 3/1992 | Bolich et al. .............................. | 424/70 |
| 5,104,646 | 4/1992 | Bolich, Jr. et al. ......................... | 8/405 |
| 5,106,609 | 4/1992 | Bolich et al. .............................. | 424/70 |
| 5,281,654 | 1/1994 | Eisenhart et al. ......................... | 524/504 |
| 5,376,146 | 12/1994 | Casperson et al. ......................... | 8/408 |
| 5,393,305 | 2/1995 | Cohen et al. .............................. | 8/406 |
| 5,478,562 | 12/1995 | Cauwet ................................... | 424/401 |
| 5,500,021 | 3/1996 | Cotteret et al. ............................. | 8/408 |
| 6,004,355 | 12/1999 | Dias et al. .................................. | 8/406 |
| 6,010,541 | 1/2000 | de la Mettrie .............................. | 8/412 |

FOREIGN PATENT DOCUMENTS

| | | | |
|---|---|---|---|
| 0 875 237 | 4/1998 | European Pat. Off. .......... | A61K 7/13 |
| WO 97 24105 | 7/1997 | WIPO .............................. | A61K 7/13 |
| WO 97 24107 | 7/1997 | WIPO .............................. | A61K 7/13 |
| WO 97/24106 | 7/1997 | WIPO . | |
| WO 98 27941 | 7/1998 | WIPO .............................. | A61K 7/13 |

OTHER PUBLICATIONS

Dr. Yves Duccini, Pollena TŚPK, Sympozjum Rohm & Haas, Warszawa, Oct. 1993, 37, 10, 13 pages.

Dr. Yves Duccini, Pollena TŚPK, Sympozjum Rohm & Haas, Warszawa, Oct. 1993, 37, 10, 13 pages [Translation].

Dr. Charles E. Jones, A Systemic Study of the Effect of Nonionic Hydrophobically–modified Ethoxylated Urethane Rheology Modifiers on Cationic Surfactants, Società Italiana di Chimica e Scienze Cosmetologiche, Nov. 25, 1993, pp. 29–44.

Rohm & Haas Co., Technical Bulletin, Developmental Rheology Modifier SA–229N, 1993, 4 pages, No Month Given.

Rohm & Haas Co., Technical Bulletin, Aculyn, Rheology Modifiers for Personal Care Applications, Liquid Thickener/Stabilizers, Mar. 1994, 2 pages.

Rohm & Haas Co., Technical Bulletin, Aculyn, Aculyn® 44 Cosmetic Grade, Rheology Modifier and Stabilizer, Jul. 1994, 8 pages.

Rohm & Haas Co., Technical Bulletin, Aculyn, Aculyn® Thickeners and Stabilizers for Personal Care, Jul. 1994, 7 pages.

Rohm & Haas Co., Technical Bulletin, Aculyn, Thickeners Applications, Mar. 1994, 2 pages.

Rohm & Haas Co., Technical Bulletin, Aculyn, Aculyn® Thickeners and Stabilizers for Personal Care, May 1995, 8 pages.

Rohm & Haas Co., Technical Bulletin, Acrysol® 44 Cosmetic Grade, Rheology Modifier and Stabilizer, 1995, 7 pages, No Month Given.

Rohm & Haas Co., Technical Bulletin, Aculyn® 44 Cosmetic Grade, Rheology Modifier and Stabilizer, Jun. 1996, 6 pages.

Rohm & Haas Co., Technical Bulletin, Aculyn, Aculyn® Thickeners and Stabilizers for Personal Care, May 1996, 7 pages.

Rohm & Haas Co., Technical Bulletin, Aculyn, Aculyn® 46, Two–part Oxidative Hair Dye, Apr. 1997, 2 pages.

Rohm & Haas Co., Technical Bulletin, Aculyn® 46 Cosmetic Grade, Rheology Modifier and Stabilizer, Aug. 1997, 8 pages.

*Primary Examiner*—Yogendra Gupta
*Assistant Examiner*—Brian P. Mruk
*Attorney, Agent, or Firm*—Charles J. Zeller

[57] ABSTRACT

The present invention describes a two-part oxidative hair dye composition which comprises in one or both component parts at least one polyether polyurethane in combination with at least one cationic conditioning agent. The two component parts of the composition comprise a dye component composition, which includes primary intermediates and couplers, and a developing component composition, which includes an oxidizing agent, such as hydrogen peroxide. It has surprisingly been found by the present inventors that nonionic polyether polyurethane polymers and cationic conditioning agents contained in the oxidative hair dye compositions of the present invention impart and significantly enhance additional conditioning and rheological benefits to the hair. Other components commonly used in oxidative hair dye products can be added to one or both component parts of the compositions of the present invention. After mixing the two component compositions, the resulting hair dye composition mixture is thick, conveniently applied, and provides superior rheological and conditioning properties to the hair.

30 Claims, No Drawings

6,156,076

TWO-PART HAIR DYE COMPOSITIONS CONTAINING POLYETHER POLYURETHANES AND CONDITIONING AGENTS

FIELD OF THE INVENTION

The invention relates generally to compositions and methods for preparing stable oxidative hair dye products that result in long-lasting and true color and do not adversely affect the texture and condition of the hair after application. The present invention more particularly relates to two-part aqueous oxidative hair dye compositions comprising oxidation dye precursors in one of the two component parts and an oxidizing agent in the other component part. One or both of these component parts also contains one or more polyether polyurethanes and one or more conditioning agents. The compositions of the invention may also comprise other conventionally-used hair dye additives and components.

BACKGROUND OF THE INVENTION

Oxidative hair dye colorants are essential elements in hair dyeing preparations for the permanent dyeing of human hair. The hair dyeing process is achieved, in general, by the reaction of certain primary intermediates with certain coupling compounds in the presence of a suitable oxidizing agent or compound, for example, hydrogen peroxide.

When oxidation dyes, such as those comprising primary dye intermediates and couplers, are used in the dyeing of human hair, the procedure typically involves the use of a two-part system. In general, one part can be a lotion, gel or cream formulation, which contains a variety of ingredients, including oxidation dye precursors (i.e., primary intermediates and coupling agents). The other part is a developer formulation containing a suitable oxidizing agent, e.g., hydrogen peroxide. Immediately prior to application to the hair, the two parts are mixed to form a thickened liquid solution, for example, a lotion, cream, or gel. As a consequence of the oxidizing properties of the oxidizing agent, some of the natural melanin pigment of the hair may be bleached. The oxidation dye precursors in the thickened solution (e.g., lotion or gel) penetrate into the hair, couple and are oxidized to produce the desired color. Such systems generally contain a proportion of organic solvents and surfactants and contain relatively high levels of dye precursors to produce the desired color.

In order for procedures using permanent oxidative dyes to work properly, a number of parameters and conditions are important to consider in the use of these dyes in admixture with couplers in hair color preparations for human hair. Among these are the final color and color intensity that are produced after application to the subject's hair; the wash fastness and the light fastness of the resulting dye; the resistance of the dye to perspiration; the type of hair being dyed, e.g., virgin hair or waved hair; the resistance of the dye to various hair treatments, such as permanent wave, straightening, shampooing, conditioning and rubbing. In addition, the dye must have virtually no allergenicity or dermal or systemic toxicity. Ideally, the dye product is also economical and must remain stable against the above-mentioned external influences and against chemical agents for a suitable period of time after application to the hair, for example, for at least four to six weeks, and to insure a reasonable shelf life.

The use of alkyl quaternary amines as conditioning agents in hair dye formulations has been known in the art for approximately twenty years. More recently, the use of polyquaternium compounds has provided durable conditioning properties to hair color formulations.

Highly aqueous bases as media for dyeing hair have been employed in the art (U.S. Pat. No. 4,776,855 and RE 33786). Thickening in a high aqueous base has been accomplished by adding a polyacrylic acid derivative to the peroxide developer. As a consequence, the polyacrylic acid derivative forms an insoluble mixture at the acid pH of the developer. When mixed with the alkaline dye formulation, the polyacrylic acid becomes neutralized, which leads to thickening.

Although such aqueous bases have been described for use in a conditioning hair color product (U.S. Pat. Nos. 5,376,146 and 5,393,305), there is a partial incompatibility between the conditioning agents and the polyacrylic acids. Such an incompatibility results in disadvantages to the use of polyacrylic acid derivatives combined with cationic conditioning agents, for example, quaternary amines or polymers. Specifically, some of the anionic polyacrylic acid complexes with the cationic quaternary amine or polymer, thus resulting in inefficient thickening and loss of conditioning effect.

The present invention solves the above-mentioned incompatibility problem by the use of particular nonionic polymers for thickening the two-part dye composition in combination with one or more cationic conditioning agents. The nonionic polymers will not complex with the conditioning agents, thereby resulting in more efficient thickening and conditioning of the product. These polymers, which are not known to have a conditioning effect on their own, have been newly-discovered by the present inventors to surprisingly act to enhance the conditioning effect of other conditioning agents which may be present in the product. The net result of the present invention is a hair color composition with excellent rheology and superior conditioning properties and benefits for two-part oxidative hair dye systems.

SUMMARY OF THE INVENTION

It is an object of the present invention to provide a two-part aqueous oxidative hair dye composition, the parts of which are mixed immediately before or at the time of use to form a final hair dye composition or formulation in accordance with the present invention. The final composition mixture is applied to the hair. One part of the composition comprises a dye formulation containing one or more oxidation dye precursors, including primary intermediates and couplers. The second part of the composition contains a developer formulation comprising a developer, i.e., oxidizing compound, preferably hydrogen peroxide. One or both parts of the composition also comprises at least one polyether polyurethane, such as is described in U.S. Pat. Nos. 4,180,491, 4,155,892 and 5,281,654 and at least one conditioning agent. In accordance with the present invention, the polyether polyurethane is preferably nonionic and is also preferably modified by the addition of starch. When starch-modified polyether polyurethane is utilized, one or both parts of the composition can contain a low HLB nonionic surfactant. Preferably, at least one part of the composition contains a low HLB nonionic surfactant. Rheology modifiers, e.g., surfactants, fatty alcohols, electrolytes, or mixtures thereof, may also be included in one or both parts of the composition of the present invention.

Further objects and advantages afforded by the present invention will be apparent from the detailed description and exemplification hereinbelow.

DETAILED DESCRIPTION OF THE INVENTION

The present invention provides a two-part oxidative hair dye composition (or formulation) that is mixed immediately before or at the time of application to the hair to form the final oxidative hair dye composition, i.e., the final composition. It is to be understood that, as used herein, the terms composition and formulation are considered to be interchangeable. One component of the hair dye composition of the present invention contains a dye solution containing a mixture of oxidation dye precursors, and the other component contains an oxidizing agent that initiates the oxidative coupling which forms the color. The two component formulations may both be thin, pourable liquids. Alternatively, either or both of the component formulations may be a gel, cream, or lotion. After mixing, the resulting final composition mixture imparts a visible amount of color to the hair and the rheology of the resultant mixture is such that it is easily applied to hair, sets up rapidly and does not run or drip.

In accordance with the present invention, the two-part composition comprises a polyether polyurethane, preferably a nonionic polyether polyurethane, which affords thickening properties to the composition, and a conditioning agent, preferably, a cationic conditioning agent. In addition, the polyether polyurethane polymers utilized in the compositions according to the present invention enhance the conditioning effects and thickening properties of the resultant hair dye composition so as to provide superior rheological and conditioning benefits to the user. In the two-part composition, at least one or both of the dye component and the developer component compositions contains a polyether polyurethane polymer, preferably a nonionic polyether polyurethane polymer, and/or a conditioning agent, preferably a cationic conditioning agent.

The polyether polyurethane, as described herein, is a block copolymer of polyurethane and polyethylene glycol or polypropylene glycol. A preferred polyether polyurethane for use in the compositions of the present invention is modified by the addition of starch, which forms a complex with the polymer, such as is commercially available from Rohm and Haas under the tradename Aculyn 46. Another useable and illustrative polyether polyurethane that is not modified with starch is sold by Rohm and Haas under the tradename Aculyn 44.

In accordance with the present invention, the polyether polyurethane can be present in the dye component, in the developer component, or in both components of the composition of the invention. The polyether polyurethane polymer is generally present in the final composition in an amount sufficient to impart to the composition rheological properties required for thickened oxidative hair dyes and to enhance the hair conditioning effect of the conditioning agent. More particularly, the concentration of polyether polyurethane in the composition is about 0.15% to about 1.0%, by weight, and preferably about 0.2% to about 0.5%, by weight, based on the total weight of the composition. Unless indicated otherwise, as used herein, reagent or component amounts are in % by weight (w/w), based on the total weight of the composition.

The cationic conditioning agent employed in the compositions of the present invention can be a monoalkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5. The cationic conditioning agent may be present in the dye component, in the developer component, or in both components of the composition in accordance with the present invention. The cationic conditioning agent is present in the composition in an amount of about 0.1% to about 10%, preferably about 0.5% to about 5%. In addition, other conditioning agents, for example, amodimethicone, can be employed in the compositions of the present invention.

If the polyether polyurethane is starch-modified, it is highly preferred to include at least one surfactant in the composition. Such surfactant is preferably a nonionic surfactant, more preferably a surfactant having a low hydrophilic lipophilic balance (HLB) value (for HLB values and molecular formulae, see *Encyclopedia of Surfactants*, compiled by Michael and Irene Ash, Chemical Publishing Company, New York, N.Y., 1980 and *McCutcheon's Emulsifiers and Detergents*, McCutcheon Division, MC Publishing Company, Glen Rock, N.J., 1987). Nonlimiting examples of suitable low HLB nonionic surfactants include nonoxynol-1, nonoxynol-4, undecyth-5, laureth-2, laureth-3, ceteareth-3, ceteareth-4, ceteareth-5, $C_{12}$–$C_{15}$ Pareth-3 (Neodol 25-3) and $C_{12}$–$C_{15}$ Pareth-7 (Neodol 25-7). The nonionic, low HLB surfactant may be present in the dye part of the composition, or in the developer part of the composition, or in both. Surfactant may also be present in the same part of the composition as the starch-modified polyether polyurethane, or it may be included in the other part of the composition.

The composition of the present invention is aqueous based. Water serves as a solvent for the dyes and for many of the other ingredients comprising the dye composition. Typically, the amount of water in the final composition is about 30% to about 90%, and preferably about 50% to about 70%. Water is present in either, or both, the developer component or the dye component.

The developer component of the composition of the present invention includes an oxidizing agent which initiates the oxidative coupling reaction that forms the color of the dye formulation. Hydrogen peroxide is preferred; however, other peroxides may be suitably employed. These include, for example, urea peroxide, melamine peroxide, perborates and percarbonates, such as sodium perborate or sodium percarbonate. The oxidizing agent is present in the composition mixture in an amount of about 1% to about 6%, and preferably about 2% to about 3%.

In addition to the above-described ingredients, the dye component composition comprises one or more oxidation dye precursors, which include one or more primary dye intermediates and one or more dye couplers. The precursors are present in amounts such that, in the presence of an oxidizing agent, they react to produce an oxidative hair dye in a tinctorially effective amount for the dyeing of strands of hair.

Included among the suitable dye components that may be considered for use as primary intermediates and/or couplers in the compositions of the present invention are the following: p-phenylenediamine derivatives such as: p-toluenediamine; p-phenylenediamine; 2-chloro-p-phenylenediamine; N-phenyl-p-phenylenediamine; N-2-methoxyethyl-p-phenylenediamine; N,N-bis-hydroxyethyl-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-bis-(N-hydroxyethyl)-N-(4-aminophenyl)amino)-2-propanol; and 2-methyl4-dimethylaminoaniline, or combinations thereof.

Preferred p-phenylenediamine derivatives include: p-toluenediamine; p-phenylenediamine; N-2-methoxyethyl-p-phenylenediamine; N,N-bis-hydroxyethyl-p-phenylenediamine; and 2-hydroxyethyl-p-phenylenediamine.

p-Aminophenol derivatives include: p-aminophenol; p-methylaminophenol; 3-methyl-p-aminophenol; 2-hydroxymethyl-p-aminophenol; 2-methyl-p-aminophenol; 2-(2'-hydroxyethylaminomethyl)-p-aminophenol; 2-methoxymethyl-p-aminophenol; and 5-aminosalicylic acid, or combinations thereof.

Preferred p-aminophenol derivatives include: p-aminophenol; p-methylaminophenol; 3-methyl-p-aminophenol; 2-methyl-p-aminophenol; 2-(2'-hydroxyethylaminomethyl)-p-aminophenol; 2-methoxymethyl-p-aminophenol; and 5-aminosalicylic acid.

Ortho developers include: catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; and 2-amino-5-acetaminophenol, or combinations thereof.

Preferred ortho developers include: o-aminophenol; 2,4-diaminophenol; 2,4,5-trihydroxytoluene; 1,2,4-trihydroxybenzene; 2-ethylamino-p-cresol; 5-methyl-o-aminophenol; 6-methyl-o-aminophenol; and 2-amino-5-acetaminophenol.

Phenols and resorcinol derivatives include: 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; hydroquinone; 2-methylresorcinol; 1-hydroxy-6-aminonaphthalene-3-sulfonic acid; thymol (2-isopropyl-5-methylphenol); 1,5-dihydroxy-1,2,3,4-tetrahydronaphthalene; 2-chlororesorcinol; 2,3-dihydroxy-1,4-naphthoquinone; and 1-naphthol-4-sulfonic acid, or combinations thereof.

Preferred phenols and resorcinol derivatives include: 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; hydroquinone; 2-methylresorcinol; thymol (2-isopropyl-5-methylphenol); and 2,3-dihydroxy-1,4-naphthoquinone.

m-Phenylenediamines include: m-phenylenediamine; 2-(2,4-diaminophenoxyethanol; N,N-(bis-hydroxyethyl) m-phenylenediamine; 2,6-diaminotoluene; $N^2$-bis-hydroxyethyl-2,4-diaminophenetole; bis-(2,4-diaminophenoxy)-1,3-propane; hydroxyethyl-2,4-diaminobenzene; 2-amino-4-hydroxyethylamino anisole; aminoethyloxy-2,4-diaminobenzene; 2,4-diaminophenoxyacetic acid; 4,6-(bis-hydroxyethyloxy) m-phenylenediamine; 2,4-diamino-5-methylphenetole; 2,4-diamino-5-hydroxyethyloxytoluene; 2,4-dimethoxy-1,3-diaminobenzene; and 2,6-(bis-hydroxyethylamino) toluene, or combinations thereof.

Preferred m-phenylenediamines include: m-phenylenediamine; 2,4-diaminophenoxyethanol; bis-(2,4-diaminophenoxy)-1,3-propane; hydroxyethyl-2,4-diaminobenzene; 2-amino-4-hydroxyethylamino anisole; 4,6-bis-hydroxyethyloxy-m-phenylenediamine; 2,4-diamino-5-methylphenetole; 2,4-diamino-5-hydroxyethyloxytoluene; 2,4-dimethoxy-1,3-diaminobenzene; and 2,6-(bis-hydroxyethylamino) toluene.

m-Aminophenols include: m-aminophenol; 2-hydroxy-4-carbamoylmethylamino toluene; m-carbamoylmethylamino phenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethyloxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol, or combinations thereof.

Preferred m-aminophenols include: m-aminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol.

Heterocyclic derivatives include: 2-dimethylamino-5-aminopyridine; 2,4,5,6-tetra-aminopyrimidine; 4,5-diamino-1-methyl-pyrazole; 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis-hydroxyethyloxy-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; isatin (indole-2,3-dione); 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine, or combinations thereof.

Preferred heterocyclic derivatives include: 4,5-diamino-1-methylpyrazole; 2-dimethylamino-5-aminopyridine; 2,4,5,6-tetra-aminopyrimidine; 1-phenyl-3-methyl-5-pyrazolone; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 4-hydroxyindole; 5,6-dihydroxyindole; 7-hydroxyindole; 5-hydroxyindole; 2-bromo-4,5-methylenedioxyphenol; 6-hydroxyindole; isatin (indole-2,3-dione); 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine.

Particularly illustrative among the many suitable primary intermediates suitable for use in the compositions of the present invention are p-phenylenediamine, p-toluenediamine, N,N-bis(2-hydroxyethyl)-p-phenylenediamine, 2-β-hydroxyethyl-p-phenylenediamine, p-aminophenol, 2-methyl-p-aminophenol and 3-methyl-p-aminophenol. The total concentration of primary dye intermediates in the final composition should be between about 0.0001% and about 10%, and preferably between about 0.1% and about 7%.

Particularly illustrative among the many dye couplers suitable for use in the compositions of the present invention are m-phenylenediamine, 2-(2',4'-diaminophenyl) ethanol, 1-naphthol, 2-methyl naphthol, resorcinol, 2-methylresorcinol, 2-amino-4-hydroxyethylaminoanisole, 4-amino-2-hydroxytoluene and m-aminophenol. Dye couplers may also be present in the composition of the present invention at a concentration of between about 0.0001% and about 10%, and preferably, between about 0.1% and about 7%.

In addition, the dye composition according to the present invention may contain an alkalizing agent. Suitable alkalizing agents include, but are not limited to, ammonia, monoethanolamine, aminomethylpropanol, sodium carbonate and methylethanolamine. When an alkalizing agent is employed, it is present in the composition at a concentration of between about 0.1% and about 15%, preferably between about 0.3% and about 10%. It is preferable to buffer the composition in the presence of an alkalizing agent. Nonlimiting examples of suitable buffering agents include oleic acid, dilinoleic acid, citric acid, sodium phosphate and sodium carbonate. When ammonia or an amine is employed as the alkalizing agent, an ammonium salt or amine salt is preferably used to buffer the composition. In accordance with the present invention, buffering agents are present in an amount of between about 0.1% and about 25%, and preferably between about 1% and about 10%.

After the two component compositions are mixed, the pH of the resulting composition mixture is optimally between about 6.5 and about 11. The preferable pH range for the final composition mixture is between about 8.0 and about 10.5.

It is desirable to include a rheology modifier in one or both parts of the component compositions in accordance with the present invention. Suitable rheology modifiers include, but are not limited to, alkylpolyglucosides, such as decylpolyglucoside, laurylpolyglucoside; alkyl diethanolamides (DEA), such as lauramide DEA, cocamide DEA, oleamide DEA and linoleamide DEA; and alkyl monoethanolamides (MEA), such as cocamide MEA, lauramide MEA and stearamide MEA. When employed, rheology modifiers are present in the component compositions of the present invention in an amount of between about 0.15% and about 10%, preferably between about 1.5% and about 5%.

As will be appreciated by those having skill in the art, other cosmetically acceptable components that are commonly used in permanent hair dye products may also be added to the compositions of the present invention. Such component ingredients include organic solvents, surfactants, antioxidants, fragrances and other typically used hair dye materials.

Nonlimiting examples of typical solvents include ethyl alcohol, isopropyl alcohol, propylene glycol, carbitol, glycerin and hexylene glycol. Solvents can be present in the component compositions of the present invention in an amount between about 0.5% and about 40%, preferably between about 1.0% and about 20%

Suitable surfactants for use, other than the low HLB nonionics described above, include high HLB nonionic surfactants, such as nonoxynol-9, PEG-14 laurate, or Neodol-23 (Shell Oil) and amphoteric surfactants, such as cocamidopropyl betaine, disodium cocamidopriprionate and disodium cocamphodiacetate. When employed, such surfactants are present in the final composition in an amount between about 1% and about 25%, preferably between about 3% and about 10%.

Nonlimiting examples of suitable antioxidants include erythorbic acid, ascorbic acid and sodium sulfite, which are typically present in the composition in an amount of about 0.05% to about 1%, preferably about 0.1% to about 0.5%.

Fragrances or perfumes are used to give the final hair dye composition product a pleasant odor and are typically present in the compositions in an amount of about 0.1% to about 5%, preferably at about 0.3% to about 1.5%. Other ingredients that may be added to the compositions in accordance with the present invention include metal chelating agents, such as EDTA; natural ingredients or herbals, such as chamomile, ginseng and jojoba oil; and aesthetic enhancers, such as mica and certified colors.

The present invention further embraces a method of enhancing the conditioning effect of a keratin fiber, preferably a hair fiber, more preferably a human hair fiber, in which the conditioning effect is produced by contacting the fiber with a composition containing a conditioning agent, preferably a cationic conditioning agent. The method of enhancing the conditioning effect comprises adding to the composition a conditioning enhancing amount of one or more nonionic polyether polyurethane polymers in accordance with the present invention.

EXAMPLES

The examples as set forth herein are meant to exemplify the various aspects of the present invention and are not intended to limit the invention in any way.

EXAMPLES 1–7

Two-part hair dye compositions were prepared to illustrate the oxidative hair dye products that are provided in accordance with the present invention. Constituents of the two component parts, i.e., the dye component composition and the developer component composition and their respective amounts, are set forth in Examples 1–7. Examples 1–4 represent four dye component formulations and Examples 5–7 represent three peroxide-containing developer component formulations, respectively, in accordance with the present invention. The dye component compositions are mixed with the developer component compositions to form the final conditioning oxidative hair dye composition at the time of use.

The compositions described in each of the Examples herein were prepared by the following illustrative general procedure:

To a suitable batching vessel, 75% of the total amount of water is added at 85° C. The emulsifiers, waxes and antioxidants are added with mixing. The remaining surfactants and quaternary compounds are added, one at a time, to the mixture with stirring. The dye precursors are added and are allowed to dissolve completely. Finally, the mixture is allowed to cool to 40° C. and alkalizing agent is added. Q.S. with the remaining water.

EXAMPLES 1–4

| DYE COMPONENT COMPOSITIONS IN ACCORDANCE WITH THE PRESENT INVENTION | | | | |
|---|---|---|---|---|
| | WEIGHT % | | | |
| EXAMPLE | 1 | 2 | 3 | 4 |
| INGREDIENT | | | | |
| Behentrimonium chloride | 4.0 | | | 4.5 |
| Soytrimonium chloride | | 6.5 | | |
| Polyquaternium 22 | | | 2.0 | 3.0 |

-continued

DYE COMPONENT COMPOSITIONS IN ACCORDANCE WITH THE PRESENT INVENTION

| EXAMPLE | WEIGHT % | | | |
|---|---|---|---|---|
| | 1 | 2 | 3 | 4 |
| Laureth-23 | 4.0 | 2.0 | 6.0 | 4.0 |
| Cetyl alcohol | 0.5 | | 0.5 | |
| Cocamide MEA | 2.5 | | | |
| Decylpolyglucoside | | 6.0 | | 2.9 |
| Lauramide DEA | | | 3.8 | |
| Sodium sulfite | 0.10 | 0.10 | 0.10 | 0.10 |
| Erythorbic acid | 0.40 | 0.40 | 0.20 | 0.30 |
| p-Phenylenediamine | 0.123 | 0.414 | 2.0 | 0.05 |
| N,N-bis(2-hydroxyethyl)-PPD sulfate | 0.05 | 0.20 | 1.0 | |
| p-Aminophenol | | | 0.08 | 0.40 |
| m-Aminophenol | | 0.15 | 0.15 | 0.08 |
| Resorcinol | | 0.60 | 1.40 | 0.02 |
| 1-Naphthol | 0.05 | | 0.30 | |
| Aculyn 46 | 5.0 | 2.0 | 2.0 | |
| Aculyn 44 | | | | 1.0 |
| Ammonium hydroxide | 5.0 | 4.0 | | 7.0 |
| Ethanolamine | 1.0 | 3.0 | 5.0 | |
| Water QS | 100 | 100 | 100 | 100 |

EXAMPLES 5–7

DEVELOPER (OXIDIZER) COMPONENT COMPOSITIONS IN ACCORDANCE WITH THE PRESENT INVENTION

| EXAMPLE | WEIGHT % | | |
|---|---|---|---|
| INGREDIENT | 5 | 6 | 7 |
| Hydrogen peroxide | 12.3 | 6.0 | 9.0 |
| $C_{12}$—$C_{15}$ Pareth-3 | 4 | | 3 |
| Nonoxynol-4 | | 3.5 | |
| Steareth-21 | 2 | | 2 |
| Nonoxynol-10 | | 1.4 | |
| PEG-50 tallow amide | 1 | 1 | |
| Oleth-5 | 1 | | 1 |
| Nonoxynol-9 | | 0.5 | |
| Oleyl alcohol | 0.3 | | |
| Stearyl alcohol | | 2 | |
| Cetyl alcohol | 0.5 | | 1.2 |
| Etidronic acid | To pH 3.5 | | |
| Phosphoric acid | | To pH 4.0 | To pH 4.4 |
| Simethicone | 0.002 | | 0.002 |
| Disodium EDTA | 0.04 | 0.02 | |
| Water QS | 100 | 100 | 100 |

EXAMPLES 8–15

Other two-part hair dye compositions were prepared as gel/lotion compositions in accordance with the present invention. The ingredients in the dye component compositions, and their respective amounts (% by weight of the total composition) are presented in Examples 8–15. Two developer component compositions were prepared as presented in A and B hereinbelow.

| | WEIGHT % IN DYE LOTION/GEL COMPONENT | | | | | | | |
|---|---|---|---|---|---|---|---|---|
| EXAMPLE | 8 | 9 | 10 | 11 | 12 | 13 | 14 | 15 |
| INGREDIENT | | | | | | | | |
| Behentrimonium chloride | 4 | 0 | 0 | 4.5 | 4 | 4 | 4 | 1 |
| Soytrmonium chloride | 0 | 6.5 | 0 | 0 | 0 | 0 | 0 | 4 |
| Polyquaternium 22 | 0 | 0 | 2 | 3 | 8 | 8 | 8 | 0 |
| Hydroxyethyl-cetyldimonium chloride | 0 | 0 | 0 | 0 | 0 | 0 | 0 | 1 |
| Cocamidopropyl betaine | 0 | 0 | 0 | 0 | 0 | 0 | 0 | 5 |
| Dow Corning 8379 silicone microemulsion | 0 | 0 | 0 | 0 | 0 | 0 | 0 | 3 |
| Laureth-23 | 4 | 2 | 6 | 4 | 4 | 4 | 0 | 0 |
| Oleyl alcohol | 1 | 1 | 1 | 1 | 1 | 1 | 0 | 0 |
| Cetyl alcohol | 0.5 | 0 | 0.5 | 0 | 0.5 | 0.5 | 0 | 0 |
| Nonoxynol-2 | 0 | 0 | 0 | 0 | 0 | 0 | 5 | 0 |
| Nonoxynol-4 | 0 | 0 | 0 | 0 | 0 | 0 | 10 | 0 |
| Ethoxyldiglycol | 0 | 0 | 0 | 0 | 0 | 0 | 7 | 0 |
| Hexylene glycol | 0 | 0 | 0 | 0 | 0 | 0 | 0 | 1 |
| Isopropyl alcohol | 0 | 0 | 0 | 0 | 0 | 0 | 9.5 | 0 |
| Propylene glycol | 0 | 0 | 0 | 0 | 0 | 0 | 9 | 0 |
| Cocamide MEA | 2.5 | 0 | 0 | 0 | 2.5 | 2.5 | 0 | 0 |
| Decylpolyglucose | 0 | 6 | 0 | 2.9 | 0 | 0 | 0 | 0 |
| Lauramide DEA | 0 | 0 | 3.8 | 0 | 0 | 0 | 0 | 0 |
| 28% Ammonia | 7 | 6.5 | 0 | 9 | 7 | 7 | 7 | 0 |
| Monoethanolamine | 0 | 0 | 8 | 0 | 0 | 0 | 0 | 0 |

-continued

| EXAMPLE | WEIGHT % IN DYE LOTION/GEL COMPONENT | | | | | | | |
|---|---|---|---|---|---|---|---|---|
| | 8 | 9 | 10 | 11 | 12 | 13 | 14 | 15 |
| Aminomethyl-propanol | 0 | 0 | 0 | 0 | 0 | 0 | 0 | 4 |
| Oleic acid | 0 | 0 | 0 | 0 | 0 | 0 | 7 | 0 |
| Sodium sulfite | 0.1 | 0.1 | 0.1 | 0.1 | 0.1 | 0.1 | 0.1 | 0 |
| Erythorbic acid | 0.4 | 0.4 | 0.2 | 0.3 | 0.4 | 0.4 | 0 | 0.2 |
| Aculyn-44 | 0 | 0 | 3.5 | 0 | 0 | 0 | 0 | 1.5 |
| Aculyn-46 | 1 | 1 | 0 | 1.2 | 1 | 0 | 0 | 0 |
| p-Phenylenediamine | 0.123 | 0.414 | 2 | 0.05 | 0.123 | 0.123 | 0.12 | 0.39 |
| N,N-bis(2-hydroxyethyl)-PPD sulfate | 0.06 | 0.2 | 0.9 | 0.01 | 0.06 | 0.06 | 0.06 | 0.12 |
| p-Aminophenol | 0 | 0.05 | 0 | 0.03 | 0 | 0 | 0 | 0 |
| m-Aminophenol | 0 | 0.03 | 0 | 0.01 | 0 | 0 | 0 | 0 |
| Resorcinol | 0.4 | 0.51 | 1.3 | 0.21 | 0.4 | 0.4 | 0.4 | 0.56 |
| 1-Naphthol | 0.05 | 0.09 | 0.24 | 0.02 | 0.05 | 0.05 | 0.05 | 0.08 |
| Water | 95 | 75.206 | 70.46 | 73.67 | 70.867 | 71.867 | 32.8 | 78.15 |

| | WEIGHT % IN DEVELOPER COMPONENT COMPOSITION | |
|---|---|---|
| INGREDIENT | A | B |
| Hydrogen peroxide (50%) | 12 | 12 |
| Steareth-21 | 2 | 2 |
| Nonoxynol-2 | 1 | 1 |
| Nonoxynol-4 | 3 | 1 |
| Cetyl alcohol | 0.1 | 0.1 |
| Phosphoric acid | 0.002 | 0.002 |
| Aculyn 22 | 0 | 1.2 |
| Aculyn 33 | 0 | 7 |
| Water | 81.898 | 75.698 |

EXAMPLE 16

As presented in Table 1, the dye lotion component compositions of Examples 12 and 13 were each mixed with equal parts of the developer component composition A as set forth above. Dye lotion component composition 13 was also mixed with equal parts of developer component composition B as set forth above. In addition, the dye lotion component composition of Example 14 was mixed with equal parts of developer component composition A. The resultant oxidative hair dye mixtures were used to treat tresses of brown hair. The combability of the resultant dye mixtures on the hair was measured using an Instron Device. The results are presented in Table 1.

TABLE 1

| Combability | 12 + A | 13 + A | 13 + B | 14 + A |
|---|---|---|---|---|
| Combing Before | 1540 | 1270 | 1420 | 1500 |
| Combing After | 380 | 405 | 520 | 4048 |
| Difference | 1160 | 865 | 900 | −2548 |
| % Improvement | 75.3% | 68.1% | 63.4% | −169.9% |

In Table 1, "12+A" represents a typical composition in accordance with the present invention. "13+A" is an identical composition, but without any thickener. "13+B" is also an identical composition, except that two anionic polymers are used for thickening. "14+A" is an oxidation dye composition containing the same conditioners as the other three compositions, but represents a conventional composition having a low water content and a high level of surfactants. All of the compositions contain two conditioners at the same concentrations, and it is expected that all four compositions will condition hair.

It can be seen that the surfactants and solvents of the conventional composition (14+A) interfere greatly with conditioning. The anionic polymeric thickener (13+B) also interferes with conditioning, but to a much lesser degree. The data also show that the polyether polyurethane thickener of the present invention augments the conditioning so that this composition (12+A) is better at conditioning than is composition (13+A) which has no thickener and is therefore not useful in hair color formulations. Thus, it is apparent that not only does the polyether polyurethane thickener of the present invention provide desirable rheology without interfering with conditioning, it surprisingly actually enhances the conditioning effect. This is wholly unexpected since the polyether polyurethane thickener of the present invention was not heretofore known to possess any combing improvement effect.

The contents of all patents, patent applications, published articles, books, reference manuals, texts and abstracts cited herein are hereby incorporated by reference in their entirety to more fully describe the state of the art to which the present invention pertains.

The present invention has been described in detail including the preferred embodiments thereof. However, it will be appreciated by those skilled in the art, upon consideration of this disclosure, that modifications and improvements may be made thereon without departing from the spirit and scope of the invention as set forth in the description and claims.

What is claimed is:

1. In a two part hair dye composition for the oxidative dyeing of hair, said composition comprising a first dye component composition comprising one or more primary dye intermediates and one or more coupling agents; and a second developer component composition comprising an oxidizing effective amount of an oxidizing agent, the improvement comprising at least one or both of said first and second component compositions containing a nonionic polyether polyurethane polymer and a cationic conditioning agent; the polyether polyurethane polymer being present in an amount sufficient to impart to said composition rheological properties required for thickened oxidative hair dyes and to enhance the hair conditioning effect of the cationic conditioning agent.

2. The composition according to claim 1, wherein said polyether polyurethane polymer is a block copolymer of polyurethane and polyethylene glycol or polypropyleneglycol.

3. The composition according to claim 2, wherein said polyether polyurethane polymer is polyethylene glycol-150/decyl alcohol/saturated methylene diphenyldiisocyanate copolymer.

4. The composition according to claim 1, wherein said polyether polyurethane polymer is starch-modified.

5. The composition according to claim 4, wherein said starch-modified polyether polyurethane polymer is polyethylene glycol-150/stearyl/saturated methylene diphenyldiisocyanate copolymer.

6. The composition according to claim 1, further comprising a nonionic surfactant having a low hydrophilic lipophilic balance.

7. The composition according to claim 6, wherein said nonionic surfactant is selected from the group consisting of nonoxynol-1, nonoxynol-4, undecyth-5, laureth-2, laureth-3, ceteareth-3, ceteareth-4, ceteareth-5, $C_{12}$–$C_{15}$ Pareth-3 and $C_{12}$–$C_{15}$ Pareth-7.

8. The composition according to claim 1, wherein said cationic conditioning agent is selected from the group consisting of monoalkyl quaternary amines, dialkyl quaternary amines and polyquaternium compounds.

9. The composition according to claim 1, wherein said cationic conditioning agent is selected from the group consisting of stearyltrimonium chloride, soyatrimonium chloride, coco-ethyldimonium ethosulfate, dicetyldimonium chloride, dicocodimethyl ammonium chloride, distearyldimethyl ammonium chloride, behentrimonium chloride, Polyquaternium-6, Polyquaternium-22 and Polyquaternium-5.

10. The composition according to claim 1, wherein said cationic conditioning agent is present in an amount of about 0.1% to about 10%, by weight of the total composition.

11. The composition according to claim 1, wherein said primary dye intermediate is one or more dye compounds selected from the group consisting of p-phenylenediamine, p-toluenediamine, N,N-bis(2-hydroxyethyl)-p-phenylenediamine, p-aminophenol, 2-methyl-p-aminophenol, 2-β-hydroxyethyl-p-phenylenediamine and 3-methyl-p-aminophenol.

12. The composition according to claim 1, wherein said coupling agent is one or more coupler compounds selected from the group consisting of m-phenylenediamine, 2-(2',4'-diaminophenyl)ethanol, 1-naphthol, 2-methylnaphthol, resorcinol, 2-methylresorcinol, 2-amino-4-hydroxyethylaminoanisole, 4-amino-2-hydroxytoluene and m-aminophenol.

13. The composition according to claim 1, wherein the concentration of said primary dye intermediate or said coupling agent is between about 0.0001% and about 10% by weight of the total composition.

14. The composition according to claim 1, wherein said oxidizing agent is selected from the group consisting of hydrogen peroxide, urea peroxide, melamine peroxide, sodium perborate and sodium percarbonates.

15. The composition according to claim 1, wherein said oxidizing agent is present in the final mixture in an amount of about 1% to about 6%, by weight of the total composition.

16. The composition according to claim 1, further comprising a rheology modifier in one or both component parts of said composition.

17. The composition according to claim 16, wherein said rheology modifier is selected from the group consisting of alkylpolyglucosides, alkyl diethanolamides, alkyl monoethanolamides, surfactants, fatty alcohols and electrolytes.

18. The composition according to claim 16, wherein said rheology modifier is present in an amount of about 0.5% and about 10% by weight of said total composition.

19. The composition according to claim 1, further comprising an alkalizing agent.

20. The composition according to claim 19, wherein said alkalizing agent is selected from the group consisting of ammonia, monoethanolamine, aminomethylpropanol and sodium carbonate.

21. The composition according to claim 1, further comprising an organic solvent.

22. The composition according to claim 21, wherein the organic solvent is selected from the group consisting of ethyl alcohol, isopropyl alcohol, propylene glycol, carbitol, glycerin and hexylene glycol.

23. The composition according to claim 21, wherein the solvent is present in an amount of about 0.5% and about 40%, by weight, based on the total weight of the composition.

24. The composition according to claim 23, wherein the solvent is present in an amount of about 1.0% and about 20%, by weight, based on the total weight of the composition.

25. The composition according to claim 1, further comprising an additive ingredient selected from the group consisting of surfactants, antioxidants, fragrances, chelating agents, herbals, and aesthetic enhancers.

26. The composition according to claim 1, wherein the polyether polyurethane polymer is present in an amount of about 0.15% to about 1.0%, by weight, based on the total weight of the composition.

27. The composition according to claim 26, wherein the polyether polyurethane polymer is present in an amount of about 0.2% to about 0.5%, by weight, based on the total weight of the composition.

28. The composition according to claim 1, wherein water is present in an amount of about 30% to about 90% based on the total weight of the composition.

29. The composition according to claim 28, wherein water is present in in an amount of about 50% to about 70% based on the total weight of the composition.

30. A method of oxidatively dyeing and conditioning human hair, comprising applying onto the hair a tinctorially effective amount a mixture of the two part hair dye composition according to claim 1 and maintaining contact of said mixture with the hair until the hair is dyed and conditioned.

* * * * *